| United States Patent [19] | [11] Patent Number: 4,812,573 |
| Durant et al. | [45] Date of Patent: Mar. 14, 1989 |

[54] PHARMACEUTICALLY ACTIVE COMPOUNDS

[75] Inventors: Graham J. Durant, Plymouth; Andrew D. Gribble, Knebworth; Robert A. Slater, Letchworth, all of England

[73] Assignee: SmithKline & French Laboratories, Ltd., Welwyn Garden City, England

[21] Appl. No.: 212,095

[22] Filed: Jun. 27, 1988

Related U.S. Application Data

[63] Continuation of Ser. No. 113,302, Oct. 28, 1987, abandoned.

[30] Foreign Application Priority Data

Oct. 28, 1986 [GB] United Kingdom ............... 8625739
Jun. 30, 1987 [GB] United Kingdom ............... 8715274

[51] Int. Cl.$^4$ ..................... A61K 31/47; C07D 217/04
[52] U.S. Cl. ..................... 514/307; 514/310; 546/143; 546/145; 546/146; 546/147
[58] Field of Search ............... 546/143, 145, 146, 147; 514/307, 310

[56] References Cited

U.S. PATENT DOCUMENTS

| 4,321,254 | 3/1982 | Ali ........................................ 546/143 |
| 4,350,698 | 9/1982 | Gleason et al. .................... 546/146 |
| 4,443,477 | 4/1984 | Witte et al. ........................ 544/390 |
| 4,536,510 | 8/1985 | Wasserman et al. ............... 514/308 |

Primary Examiner—Glennon H. Hollrah
Assistant Examiner—James H. Turnipseed
Attorney, Agent, or Firm—Edward T. Lentz; Janice E. Williams; Alan D. Lourie

[57] ABSTRACT

The invention relates to a class of tetrahydroisoquinolinylalkanoic acids containing an aryl sulphonamide group which have activity as thromboxane $A_2$ antagonists.

17 Claims, No Drawings

PHARMACEUTICALLY ACTIVE COMPOUNDS

This is a continuation of application Ser. No. 113,302 filed Oct. 28, 1987 now abandoned.

The present invention relates to a class of tetrahydroisoquinoline compounds containing a sulphonamido group which have activity as thromboxane $A_2$ antagonists, to the use of the compounds in medicine, to pharmaceutical compositions containing them and to methods for their preparation.

Thromboxane $A_2$ ($TXA_2$) is a potent vasoconstricting and platelet aggregating agent which is formed in platelets and other tissues as a product of the "arachidonic acid cascade". $TXA_2$ is produced by the thromboxane synthetase catalysed conversion of prostaglandin $H_2$ ($PGH_2$) which in turn is produced, via the intermediacy of prostaglandin $G_2$ ($PGG_2$), by the action of cyclooxygenase on arachidonic acid. The potency of $TXA_2$ is such that very small amounts can trigger serious biological consequences and it has been implicated in mediating pathophysiological actions in severe disorders such as circulatory shock and myocardial ischaemia.

One method of inhibiting the effects of thromboxane $A_2$ is through the selective antagonism of $TXA_2/PGH_2$ at the receptor level and various compounds have been reported as $TXA_2$ receptor antagonists, see for example U.S. Pat. No. 4,536,510 and EP No. 31954.

It has now been discovered that a class of sulphonamide-substituted isoquinolines has biological activity indicative of an ability to antagonise $TXA_2$ receptors. Accordingly, in a first aspect, the present invention provides compounds of the formula (I):

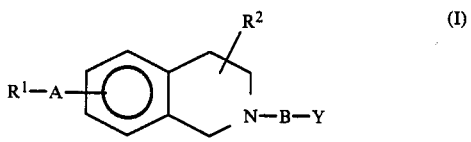

and salts thereof; wherein

A is a group $NR^3SO_2$ or $SO_2NR^3$;

B is an acyclic hydrocarbon group having from one to six linear carbon atoms, provided that the carbon atom attached to the nitrogen atom is saturated;

Y is $CO_2H$ or a group hydrolysable to $CO_2H$;

$R^1$ is phenyl optionally substituted by one or more substituents chosen from the group comprising halogen, $C_{1-4}$alkyl, $C_{1-6}$acyl, $C_{1-4}$alkoxy, nitro and trifluoromethyl;

$R^2$ is hydrogen or one or more $C_{1-4}$alkyl substituents located at the 1, 3 and 4 positions of the isoquinoline ring; and $R^3$ is hydrogen or $C_{1-6}$alkyl.

By linear carbon atoms is meant those carbon atoms extending in an unbranched chain between the nitrogen atom of the isoquinoline ring and the group Y.

By saturated is meant that the carbon atom attached to the nitrogen atom of the isoquinoline ring does not form part of a carbon-carbon multiple bond.

The acyclic hydrocarbon group B can be an alkylene group or it can contain alkene and/or alkyne groups. The group can be a straight chain or branched chain group and it will be appreciated that any one or more of the linear carbon atoms can be substituted by an alkyl group or groups. Preferably any alkyl group substituents are methyl groups.

It is preferred that the total number of carbon atoms in the hydrocarbon group does not exceed eight.

Particular alkylene groups are $C_{2-5}$ straight chain alkylene groups, preferably propane-1,3-diyl and butane-1,4-diyl, a particularly preferred group being propane-1,3-diyl.

When the hydrocarbon group contains an alkyne or alkene group, preferably there is only one unsaturated group present. A particular hydrocarbon group containing an alkyne group is prop-1-yne-1,3-diyl.

Alkene groups can have E or Z configurations and compounds having both such configurations are within the scope of the invention.

In one embodiment of the invention the terminal carbon atom in the hydrocarbon group adjacent to the group Y has a gem-dimethyl substitution pattern.

It is preferred that the carbon atom adjacent to the isoquinoline ring nitrogen forms part of the methylene ($CH_2$) group.

The group A can be located at any one of the aromatic 5-, 6-, 7- or 8-positions of the isoquinoline ring. Preferably the group A is a group $NR^3SO_2$ and particularly it is located at the 7-position of the isoquinoline ring.

The group Y hydrolysable to $CO_2H$ suitably is a nitrile, amide or ester. Examples of esters are $C_{1-6}$alkyl esters and optionally substituted benzyl esters. Particular ester groups include, for example, $C_{1-4}$alkoxycarbonyl groups such as ethoxycarbonyl and methoxycarbonyl. Amide groups Y include carbamoyl, mono-$C_{1-6}$alkylcarbamoyl and di-$C_{1-6}$alkylcarbamoyl groups such as N-methylaminocarbonyl and N,N-dimethylaminocarbonyl.

Suitably $R^1$ represents a phenyl group having up to two substituents. Preferably the phenyl group is unsubstituted or there is only a single substituent. Preferred positions of substitution are the 3- and 4-positions of the phenyl ring.

Examples of $C_{1-6}$acyl substituents are $C_{1-6}$alkanoyl, $C_{1-6}$alkoxycarbonyl and carbamoyl.

Particular examples of the group $R^1$ are unsubstituted phenyl or phenyl substituted by chloro, bromo, methyl, trifluoromethyl and methoxy, a most particular example being phenyl substituted with chloro, particularly 3-chloro or 4-chloro.

Examples of the group $R^2$ are hydrogen, methyl and ethyl, particularly hydrogen.

Suitably $R^3$ is hydrogen or methyl, particularly hydrogen.

One particular group of compounds of the present invention is represented by the general formula (II):

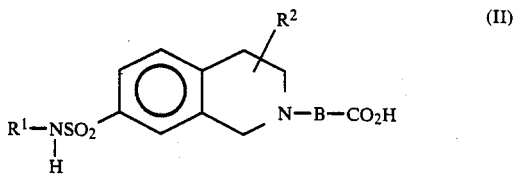

wherein $R^1$, $R^2$ and B are as defined above.

Particular and preferred groups B, $R^1$ and $R^2$ for compounds of the formula (II) are as defined above in respect of compounds of the formula (I).

Preferred compounds of the present invention are 4-[7-(3-chlorophenylsulphamoyl)-1,2,3,4-tetrahydroisoquinolin-2-yl]butanoic acid;

5-[7-(3-chlorophenylsulphamoyl)-1,2,3,4-tetrahydroisoquinolin-2-yl]pentanoic acid; and 4-[7-(3-chlorophenylsulphamoyl)-1,2,3,4-tetrahydroisoquinolin-2-yl]but-1-ynoic acid.

Compounds of the formula (I) can form several different types of salt but preferred salts are acid addition salts, formed by interaction of the nitrogen atom of the isoquinoline ring with an appropriate proton acid, and carboxylate salts formed by interaction of the carboxylic acid group with an appropriate base. Compounds of the formula (I) can exist in zwitterionic form and such forms are also within the scope of the invention.

Examples of acid addition salts are those formed by interaction of a compound of the formula (I) with an acid selected from hydrochloric, sulphuric, phosphoric, acetic, methanesulphonic, ethanesulphonic, isethionic, glucuronic, lactobionic, toluenesulphonic, benzenesulphonic, naphthalenesulphonic, hydrobromic, tartaric, citric, maleic, lactic, and camphorsulphonic acids.

Examples of carboxylate salts are alkali metal, alkaline earth metal and ammonium salts. Alkali and alkaline earth metal salts typically are formed by interaction of a carboxylic acid with a metal alkoxide or hydroxide whereas ammonium salts typically are formed by interaction of the carboxylic acid with the appropriate amine or the appropriate ammonium hydroxide.

It is preferred that the salts are pharmaceutically acceptable, although non-pharmaceutical salts are also within the scope of the invention. Such salts can be converted into pharamceutically acceptable salts or into the corresponding free base or free acid.

Compounds of formula (I) can also exist as solvates, for example hydrates and alcoholates, and all such forms are within the scope of the invention.

Compounds of the formula (I) wherein Y is $CO_2H$ or a $C_{1-4}$alkoxycarbonyl group such as ethoxycarbonyl have activity as thromboxane-$A_2$ receptor antagonists. Other compounds of the formula (I) wherein Y is a group hydrolysable to $CO_2H$ primarily useful as chemical intermediates, unless metabolised by mammals to compounds wherein Y is $CO_2H$ in which case they can function as pro-drugs.

The present invention also provides a process for preparing compounds of the formula (I) which process comprises:

(i) the reaction of a compound of the formula (III):

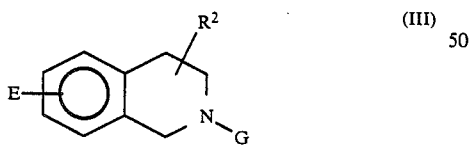

wherein

E is amino or a group $SO_2L$;

$R^2$ is as defined above;

G is an amine-protecting group or a group B-Y; and

L is a leaving group;

with a compound of the formula $R^1M$ wherein M is amino or a group $SO_2L$, provided that one of E and M is $SO_2L$ and the other is amino; and when G is an amine-protecting group removing this and reacting the compound thus formed with an alkylating agent suitable for introducing the group B-Y; or (ii) the reaction of a compound of the formula (IIIA):

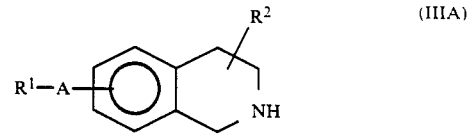

wherein $R^1$, $R^2$ and A are as hereinbefore defined, with an alkylating agent suitable for introducing the group B-Y; and thereafter, where necessary, hydrolysing Y to give $CO_2H$; and optionally converting one compound of the formula (I) into another compound of the formula (I).

Examples of leaving groups L are the halogens, particularly chlorine.

Typically the amine-protecting group is an acyl group, for example the acyl residue of a $C_{1-6}$alkanoic acid or optionally substituted benzoic acid. A particular protecting group is acetyl.

The alkylating agent typically is a compound of the formula $L^1$-B-Y wherein $L^1$ is a leaving group such as a halogen, particularly bromine.

When it is required to prepare a compound wherein B is $(CH_2)_2$, the alkylating agent can also be selected from compounds of the formula $H_2C=CH-Y$ wherein Y is as defined above.

The reaction of compounds of the formula (III) with compounds of the formula $R^1M$ suitably is conducted in a polar solvent, usually aprotic and preferably dry, such as dry acetone or dichloromethane, with heating where required, for example at the reflux temperature of the solvent. The reaction typically is conducted in the presence of another base such as pyridine or a trialkylamine such as triethylamine.

When it is desired to prepare a compound of the formula (I) wherein $R^3$ is a $C_{1-6}$alkyl group, the amino group E or M in the compound of the formula (III) or $R^1M$ can be a group $NHR^3$. Alternatively, a compound of the formula (I) wherein $R^3$ is $C_{1-6}$alkyl can be prepared by reaction of the corresponding compound wherein $R^3$ is hydrogen with an alkylating agent in the presence of a base.

Compounds of the formula (III) where E is $SO_2L$ can be prepared from compounds of the formula (IV):

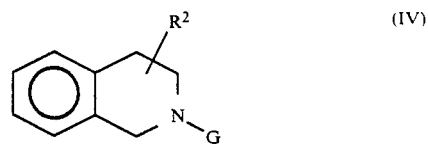

according to known methods analogous thereto, see for example European Patent Application No. 0038177.

Thus, for example, a chlorosulphonyl group can be introduced into the 7-position of a compound of the formula (IV) by reaction with chlorosulphonic acid in a halocarbon solvent such as dichloromethane. When it is required to introduce a chlorosulphonyl group in a position other than the 7-position, this can suitably be achieved by forming the appropriate mercaptotetrahydroisoquinoline and then reacting it with chlorine in glacial acetic acid.

Compounds of the formula (III) wherein E is amino can be prepared according to methods described in European patent application No. 0049135.

When the product of the reaction between compounds of the formula (III) and R¹M is a compound wherein G is an amine-protecting group, the protecting group can be removed by methods known per se; for example when G is acetyl, it can be removed by heating with hydrochloric acid in an alkanol such as n-BuOH suitably at the reflux temperature of the solvent mixture.

Compounds of the formula (IIIA) can be prepared by the reaction of a compound of the formula (III), wherein G is an amine-protecting group, with a compound of the formula R¹M followed by removal of the amine-protecting group, according to methods described hereinabove. Alternatively, compounds of the formula (IIIA) can be prepared by reduction of a compound of the formula (IIIB):

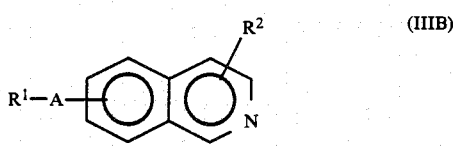

for example by hydrogenation over a transition metal catalyst such as a platinum oxide catalyst.

The tetrahydroisoquinolines resulting from the reduction of compounds of the formula (IIIB) or the reaction of a compound of the formula (III, G=amine protecting group) with a compound R¹M, followed by removal of the amine protecting group, can be alkylated suitable by treatment with an alkylating agent in a polar solvent such as an alkanol, e.g. ethanol; acetonitrile, dimethylformamide or tetrahydrofuran. Typically, the alkylation reaction is carried out in the temperature range from 0° C. to 100° C., for example at room temperature to 60° C.

Optionally a second base can be employed, for example a trialkylamine such as triethylamine, or pyridine, or an alkali metal carbonate or bicarbonate such as potassium carbonate and sodium carbonate.

When the group Y is a group hydrolysable to $CO_2H$, the hydrolysis conditions employed will depend upon the precise nature of the group but generally the hydrolysis is achieved by treating with either an aqueous mineral acid such as hydrochloric or sulphuric acids or an alkali such as sodium hydroxide, with heating as required.

Compounds of the formula (I) are useful in the treatment of conditions and diseases in which $TXA_2$ is a factor. Thus, for example, they would be useful in the treatment of conditions and disorders in which aggregation of blood platelets and vasoconstriction play a part.

Particular clinical indications in which the present compounds would be of interest include the treatment or management of post myocardial infarction, coronary thromboses (e.g. in combination with tissue plasminogen activator and other thrombolytics), unstable angina, transient ischaemia, coronary artery bypass grafts, cardiac valve replacement and peripheral and vascular grafts including for example renal transplants.

The compounds of the formula (I) can be administered as the pure compound but it is more usual to administer them as part of a pharmaceutical composition in association with a carrier and one or more excipients. In a further aspect, therefore, the present invention provides a pharmaceutical composition comprising a compound of the formula (I) and a pharmaceutically acceptable carrier.

The compositions can be administered in standard manner, for example orally, parenterally, transdermally, rectally, via inhalation or via buccal administration.

Compounds of formula (I) and their pharmaceutically acceptable salts which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil. Such compositions can be administered, for example, by bolus injection or by infusion.

A typical suppository formulation comprises a compound of formula (I) or a pharmaceutically acceptable salt thereof which is active when admistered in this way, with a binding and/or lubricating agent, for example polymeric glycols, gelatins, cocoa-butter or other low melting vegetable waxes or fats.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

Each such dosage unit suitably contains from 1 mg to 1 g, preferably from 5 mg to 500 mg, e.g. 100 mg or 200 mg, of a compound of the formula (I) or a pharmaceutically acceptable salt thereof calculated as the compound itself.

The quantity of drug administered to a patient per day will depend upon the particular condition or disease under treatment and its severity, and ultimately will be at the discretion of the physician. However, the amount administered will be a non-toxic amount effective to treat the condition in question.

A typical daily dosage regimen is 10 mg to 1 g for an average human weighing approximately 70 kg, administered in 1 to 4 dosage units, preferably 1 or 2.

The compositions of this invention, in addition to containing a comound of the formula (I) can also contain other agents; for example one or more agents chosen from phosphodiesterase inhibitors, hypolipidemic agents, platelet aggregation inhibitors, vasodilators, β-adrenergic receptor blockers, ACE inhibitors, tissue plasminogen activator and other thrombolytics, and antiarrhythmics.

The compositions of the present invention are prepared by bringing the active constituent into association with a pharmaceutically acceptable carrier and optionally other excipients and ingredients as defined above.

As indicated above, compounds of the formula (I) have biological activity that is indicative of an ability to antagonise $TXA_2$ receptors. The $TXA_2$ antagonist activity has been demonstrated in the following tests:

(a) human platelet binding assay;
(b) human platelet aggregation assay.

The platelet binding assay used was essentially the method described by Mais et al, *J. Pharm. Exp. Ther.*, 1985, 235(3), 729–734 where [$^{125}$I]PTA-OH was used as the receptor ligand.

The $IC_{50}$ values represent the concentration which produces a 50% inhibition of specific [$^{125}$I]PTA-OH binding.

HUMAN PLATELET AGGREGATION ASSAY

The aggregation assay used human washed platelets and was based on that described by Born (*Nature*, 1962, vol. 194, 927–929). The assay determines a concentration of test compound which inhibits a submaximal U46619 induced aggregation by 50% ($IC_{50}$). U46619 is the thromboxane $A_2$-agonist (9,11-dideoxy-11α,9α-epoxymethanoprostaglandin $F_{2\alpha}$).

The activities of the compounds of the present invention in the above assays are described in Example 17.

The following Examples are illustrative of the invention.

In the Examples, all temperatures are in °C. Melting points are uncorrected and were obtained in an open capillary tube using a Büchi 510 Melting Point Apparatus.

EXAMPLE 1

3-[7-(3-Chlorophenylsulphamoyl)-1,2,3,4-tetrahydroisoquinolin-2-yl]propionic acid (a)

A mixture of 7-(3-chlorophenylsulphamoyl)-1,2,3,4-tetrahydroisoquinoline hydrochloride (3.25 g, 9 mmol) (EP No. 0038177-A) and ethyl acrylate (0.91 g, 9 mmol) in THF (8 ml) was heated under reflux for 18 hr. Concentration and chromatography (silica gel, ether) gave ethyl-3-[7-(3-chlorophenylsulphamoyl)-1,2,3,4-tetrahydroisoquinolin-2-yl]propionate as a viscous oil (4.09 g, 98.7%).

(b)

A mixture of ethyl-3-[7-(3-chlorophenylsulphamoyl)-1,2,3,4-tetrahydroisoquinolin-2-yl]propionate (4.08 g) and 10% sodium hydroxide solution (10 ml) in ethanol (10 ml) was stirred at room temperature for one hour. Ethanol was removed in vacuo, water (15 ml) added and the pH was adjusted to 6–7 with 2N HCl. This was extracted with ethylacetate:methanol 4:1 (3×50 ml) and dried (MgSO$_4$). Concentration and crystallization from ethanol-methanol gave 3-[7-(3-chlorophenylsulphamoyl)-1,2,3,4-tetrahydroisoquinolin-2-yl]propionic acid. 1.2H$_2$O, 0.8NaCl (1.61 g, 59%); mpt. 137°–40° C.

$C_{18}H_{19}ClN_2O_4S.1.2H_2O$ 0.8NaCl: Found: C 46.24, H, 4.34, N 5.88, Cl 13.40. Requires: C 46.67, H, 4.66, N 6.05, Cl 13.78.

EXAMPLE 2

4-[7-(3-Chlorophenylsulphamoyl)-1,2,3,4-tetrahydroisoquinolin-2-yl]butyric acid (a) A mixture of 7-(3-chlorophenylsulphamoyl)-1,2,3,4-tetrahydroisoquinoline hydrochloride (3.05 g, 8 mmol), ethyl-4-bromobutyrate (1.56 g), and triethylamine (0.81 g, 8 mmol) in acetonitrile (35 ml) was heated at 55°–60° for 4 hr. The mixture was filtered, the filtrate concentrated and chromatographed (silica gel, ether) to give ethyl-4-[7-(3-chlorophenylsulphamoyl)-1,2,3,4-tetrahydroisoquinolin-2-yl]butyrate (0.59 g, 17%) as an oil.

(b) A mixture of ethyl-4-[7-(3-chlorophenylsulphamoyl)-1,2,3,4-tetrahydroisoquinolin-2-yl]butyrate (0.59 g, 1.35 mmol) and 10% NaOH solution (4 ml) in ethanol (10 ml) was stirred for 1 hr. Ethanol was removed in vacuo, water added (10 ml) and the pH adjusted to 6 with 2N HCl. The resulting precipitate was crystallized from methanol-water to give 4-[7-(3-chlorophenylsulphamoyl)-1,2,3,4-tetrahydroisoquinolin-2-yl]butyric acid. 0.4H$_2$O (0.44 g, 80%); mpt. 201°–203° C.

$C_{19}H_{21}ClN_2O_4S.0.4H_2O$: Found: C 54.67, H 5.16, N 6.59, S 7.66, Cl 8.84. Requires: C 54.84, H 5.28, N 6.73, S 7.71, Cl 8.52.

By following the procedure of Example 2, but substituting the appropriate ethyl-ω-bromoalkanoate for ethyl-4-bromobutyrate, the compounds of Examples 3 and 4 were prepared.

EXAMPLE 3

5-[7-(3-Chlorophenylsulphamoyl)-1,2,3,4-tetrahydroisoquinolin-2-yl]valeric acid (a) 7-(3-Chlorophenylsulphamoyl)-1,2,3,4-tetrahydroisoquinoline was reacted with ethyl 5-bromovalerate under conditions analogous to those described in Example 2(a). The crude product of the alkylation reaction was then treated with ethereal HCl, and the following ethyl ester hydrochloride was obtained; ethyl-5-[7-(3-chlorophenylsulphamoyl)-1,2,3,4-tetrahydroisoquinolin-2-yl]valerate hydrochloride; mpt. 178°–180° C. (from ethanol).

$C_{22}H_{27}ClN_2O_4S.HCl$: Found: C 54.54, H 5.79, N 5.70, Cl 14.47, S 6.4. Requires: C 54.21, H 5.79, N 5.75, Cl 14.55, S 6.58.

(b) 5-[7-(3-Chlorophenylsulphamoyl)-1,2,3,4-tetrahydroisoquinolin-2-yl]valeric acid; mpt. 176°–8° C.

$C_{20}H_{23}ClN_2O_4S$: Found: C 56.74, H 5.52, N 6.54, S 7.27, Cl 8.68. Requires: C 56.80, H 5.48, N 6.62, S 7.58, Cl 8.38.

EXAMPLE 4

6-[7-(3-Chlorophenylsulphamoyl)-1,2,3,4-tetrahydroisoquinolin-2-yl]hexanoic acid, 0.5C$_2$H$_5$OH, 0.4H$_2$O mpt. 84°–85.5° C.

$C_{21}H_{25}ClN_2O_4S$, 0.5C$_2$H$_5$OH, 0.4H$_2$O: Found: C 56.65, H 6.21, N 5.89, S 7.66, Cl 6.47. Requires: C 56.56, H 6.21, N 6.00. S 7.59, Cl 6.86.

EXAMPLE 5

4-(7-Phenylsulphamoyl-1,2,3,4-tetrahydroisoquinolin-2-yl)butyric acid (a) A mixture of 7-(phenylsulphamoyl)-1,2,3,4-tetrahydroisoquinoline hydrochloride (3 g, 9.3 mmol), ethyl-4-bromobutyrate (1.8 g, 9.3 mmol) and triethylamine (1.9 g, 18.6 mmol) in acetonitrile (45 ml) was heated at reflux for 4 hr. The mixture was filtered, the filtrate was concentrated and chromatographed (silica gel, 15:1 ethyl acetate:methanolic ammonia) to give ethyl-4-(7-phenylsulphamoyl)-1,2,3,4-tetrahydroisoquinolin-2-yl)butyrate as an oil.

(b) The product of Example 5(a) was hydrolysed according to the method described in Example 2(b) to give 4-(7-phenylsulphamoyl-1,2,3,4-tetrahydroisoquinolin-2-yl)butyric acid. mpt. 190°–191° C.

$C_{19}H_{22}N_2O_4S.0.4H_2O$: Found: C 59.44, H 5.64, N 7.02, S 8.31. Requires: C 59.79, H 6.02, N 7.34, S 8.40.

EXAMPLE 6

5-(7-Phenylsulphamoyl-1,2,3,4-tetrahydroisoquinolin-2-yl)valeric acid 7-(Phenylsulphamoyl)-1,2,3,4-tetrahydroisoquinoline hydrochloride was reacted with ethyl-5-bromovalerate under conditions analogous to those described in Example 5 and the resulting ethyl ester was hydrolysed according to the method described in Example 2(b) to give 5-(7-phenylsulphamoyl-1,2,3,4-tetrahydroisoquinolin-2-yl)valeric acid as a colourless microcrystalline solid. mpt. 176°–176.5° C. (acetonitrile/ethanol).

$C_{20}H_{24}N_2O_4S.0.5H_2O$: Found: C 60.68, H 6.09, N 7.09, S 7.85. Requires: C 60.43, H 6.34, N 7.05, S 8.07.

EXAMPLE 7

4-[7-(3-Trifluoromethylphenylsulphamoyl)-1,2,3,4-tetrahydroisoquinolin-2-yl]butyric acid 2-Acetyl-7-chlorosulphonyl-1,2,3,4-tetrahydroisoquinoline was reacted with 3-trifluoromethylaniline in dichloromethane according to the method generally described in EP No. 0038177-A. The resulting product was deacetylated by heating with aqueous hydrochloric acid in butanol to give 7-(3-trifluoromethylphenylsulphamoyl)-1,2,3,4-tetrahydroisoquinoline as the hydrochloride salt.

The hydrochloride salt was reacted with ethyl-4-bromobutyrate according to the method described in Example 5 and the resulting ester in turn was hydrolysed according to the method described in Example 2(b) to give 4-[7-(3-trifluoromethylphenylsulphamoyl)-1,2,3,4-tetrahydroisoquinolin-2-yl]butyric acid as a white crystalline solid. mpt. 163°–165° C.

$C_{20}H_{21}F_3N_2O_4S$: Found: C 54.16, H 4.76, N 6.24, S 7.11. Required: C 54.29, H 4.78, N 6.33, S 7.25.

EXAMPLE 8

Sodium 4-[7-(3-chlorophenylsulphamoyl)-1,2,3,4-tetrahydroisoquinolin-2-yl]but-2-ynoate To a mixture of 7-(3-chlorophenylsulphamoyl)-1,2,3,4-tetrahydroisoquinoline hydrochloride (3.59 g, 10 mmol) and triethylamine (2.02 g, 20 mmol) in dry acetonitrile (50 ml) was added dropwise a solution of chlorotetrolic acid (1.19 g, 10 mmol) in dry acetonitrile (20 ml). After 18 hr. the mixture was concentrated in vacuo, water was added and the pH was adjusted to ca. 10 with sodium hydroxide solution. The resulting gum was chromatographed (silica gel, 1:1 methanol:chloroform, 2×) to give the desired product, contaminated with the amine starting material, in two batches (total 1.44 g, ca. 33% yield). Further chromatography (silica gel, 10% $CH_3OH/CHCl_3$ rising to 50% $CH_3OH/CHCl_3$) gave an oil (1 g) which was triturated with isopropanol to give sodium 4-[7-(3-chlorophenylsulphamoyl)-1,2,3,4-tetrahydroisoquinolin-2-yl]but-2-ynoat (400 mg) which was further purified by recrystallisation from n-propanol. mpt.>270° C.

$C_{19}H_{16}ClN_2O_4SNa$, $1.3H_2O$, 0.1 Propanol: Found: C 50.70 H 4.00 N 6.13. Requires: C 50.77 H 4.28 N 6.13.

EXAMPLE 9

4-[5-(Phenylsulphonamido)-1,2,3,4-tetrahydroisoquinolin-2-yl]butyric acid hydrochloride (a) A solution of 5-aminoisoquinoline (20 g) in glacial acetic acid (500 ml) was shaken under hydrogen in the presence of a platinum oxide catalyst (2.0 g) at room temperature and approximately 345 kilopascals pressure until uptake of hydrogen stopped. The catalyst was removed by filtration and the filtrate was evaporated to a small volume under reduced pressure. Residual solvent was removed by co-evaporation with water, then isopropyl alcohol, and the resulting solid was recrystallized from isopropyl alcohol to give 5-amino-1,2,3,4-tetrahydroisoquinoline as a white solid, 19 g, m.p. 153°–154° C.

(b) A stirred mixture of 5-amino-1,2,3,4-tetrahydroisoquinoline (10.0 g) isopropenyl acetate (7.2 g) and ethyl acetate (150 ml) was heated under reflux for 24 hours. The cooled, filtered solution was evaporated under reduced pressure to a small volume. The residual oil was purified by elution from a silica column with ethyl acetate/methanol mixtures followed by crystallisation from ethyl acetate to give 2-acetyl-5-amino-1,2,3,4-tetrahydroisoquinoline as a white solid 6.6 g, m.p. 107°–108° C.

(c) To a stirred solution of 2-acetyl-5-amino-1,2,3,4-tetrahydroisoquinoline (6.6 g) in a mixture of dry pyridine (3 g) and dichloromethane (450 ml) at approximately 5° C. was added dropwise, over 15 minutes, benzenesulphonyl chloride (6.2 g). The orange solution was stirred overnight at room temperature and was then washed several times with water, dried and the solvent was then evaporated to give a dark orange oil. Crystallisation from 2-propanol gave 2-acetyl-5-phenylsulphonamido-1,2,3,4-tetrahydroisoquinoline as a pale pink solid (9.5 g) m.p. 131°–132° C.

(d) A stirred mixture of 2-acetyl-5-phenylsulphonamido-1,2,3,4-tetrahydroisoquinoline (9.4 g), hydrochloric acid (140 ml, 3.0M) and n-butanol (14 ml) was heated under reflux for 6 hours. The solvents were evaporated under reduced pressure and the residue was recrystallised from ethanol to give 5-phenylsulphonamido-1,2,3,4-tetrahydroisoquinoline hydrochloride as a white solid (7.8 g) m.p. 209°–21° C.

(e) 5-Phenylsulphonamido-1,2,3,4-tetrahydroisoquinoline hydrochloride (2.7 g) was reacted with ethyl 4-bromobutyrate in the manner described in Example 2(a). After elution from a silica column with ethyl acetate:methanol mixtures, the product was recrystallised from ethanol to give ethyl 4-[5-phenylsulphonamido-1,2,3,4-tetrahydroisoquinolin-2-yl]butyrate as a white solid (2.0 g).

(f) Ethyl 4-(5-phenylsulphonamido-1,2,3,4-tetrahydroisoquinolin-2-yl)butyrate was hydrolysed with sodium hydroxide solution by the method described in Example 2(b) and the product was recrystallised from methanol:ethyl acetate to give the title compound (0.6 g) m.p. 187.5°–188.5° C.

EXAMPLE 10

5-[(5-Phenylsulphonamido)-1,2,3,4-tetrahydroisoquinolin-2-yl]valeric acid hydrochloride (a) 5-Phenylsulphonamido-1,2,3,4-tetrahydroisoquinoline hydrochloride (2.2 g) was reacted with ethyl 5-bromovalerate in the manner described in Example 2(a) to give, after elution from a silica column with ethylacetate:methyl mixtures, ethyl 5-(5-phenylsulphonamido-1,2,3,4-tetrahydroisoquinolin-2-yl)valerate as a viscous yellow oil (1.7 g).

(b) Ethyl 5-(5-phenylsulphonamido-1,2,3,4-tetrahydroisoquinolin-2-yl)valerate (1.6 g) was hydrolysed with sodium hydroxide solution by the method described in Example 2(b) and the product was recrystallised from isopropanol:methanol to give the title compound (0.4 g), m.p. 217°–218° C.

EXAMPLE 11

4-[6-Phenylsulphonamido-1,2,3,4-tetrahydroisoquinolin-2-yl]butyric acid (a) Formaldehyde solution (20%) (50 g) was added dropwise with stirring to 3-methoxyphenethylamine (50 g, 0.33M) over 15 minutes. The reaction was then heated for 1 hour on a steam bath. Excess concentrated hydrochloric acid was added and the mixture was then evaporated to dryness in vacuo. The residual solid was recrystallised from MeOH:isopropanol:ether to yield 6-methoxy-1,2,3,4-tetrahydroisoquinoline hydrochloride (41 g, 61%), m.p. 234°–5° C. (lit.* 233°–4° C.).
*Helfer, Helv. Chim. Acta. 1924, 7, 945-50.

(b) 6-Methoxy-1,2,3,4-tetrahydroisoquinoline hydrochloride (41 g) was dissolved in $H_2O$, basified with aqueous KOH solution and extracted with $CHCl_3$. The $CHCl_3$ extracts were dried over $MgSO_4$ and evaporated to dryness to yield 33 g of 6-methoxy-1,2,3,4-tetrahydroisoquinoline base (0.2M). The base (33 g, 0.2M) and Palladium Black (1.5 g) were mixed together and heated at 160°–190° C. for 6 hours. The cooled reaction mixture was extracted with MeOH and the Palladium Black was filtered off. The MeOH was evaporated to dryness and the residue was chromatographed in $CHCl_3$ on silica gel column. Fractions containing product were combined and evaporated to yield 6-methoxyisoquinoline as an oil (16 g, 50%).

(c) 6-Methoxyisoquinoline (16 g, 0.1M) and 48% aqueous HBr (600 ml) were refluxed together for 6 hours and the mixture was then evaporated to dryness in vacuo. The residue was dissolved in $H_2O$ and basified with solid $Na_2CO_3$. The resulting precipitated solid was filtered off and recrystallised from isopropanol to give 6-hydroxyisoquinoline (12 g, 82%), m.p. 218°–20° C. (lit.* 220° C.).
*Osborn et al., J. Chem. Soc., 1956, 4203.

(d) 6-Hydroxyisoquinoline (12 g, 0.083M) was suspended in 180 ml $H_2O$ and $SO_2$ gas was passed through until 12 g had been absorbed. 0.880 $NH_4OH$ (240 ml) was then added and the mixture was heated in a Berghof pressure vessel for 15 hours at 150° C. (pressure approximately 730 kilopascals). After cooling the product which crystallised out was filtered off and recrystallised from benzene/60–80 pet. ether to give 6-aminoisoquinoline (7.98 g, 67%), m.p. 217°–8° C. (lit.* 217°–8° C.).
*Manske & Kulka, J. Amer. Chem. Soc., 1950, 72, 4997.

(e) Benzenesulphonyl chloride (4.9 g, 0.028M) in $CH_2Cl_2$ (15 ml) was added dropwise over 10 minutes to a cooled stirred mixture of 6-aminoisoquinoline (4.0 g, 0.028M) and pyridine (2.37 g, 0.03M) in $CH_2Cl_2$ (150 ml). The reaction mixture was stirred overnight at room temperature and was then washed with $H_2O$. The $CH_2Cl_2$ solution was dried over $MgSO_4$ and was then chromatographed on a silica gel column. After evaporation the residue was recrystallised from isopropanol to yield 6-phenylsulphonamidoisoquinoline (2.28 g, 33%), m.p. 204°–6° C.

(f) A solution of 6-phenylsulphonamidoisoquinoline (2.11 g, 0.0074M) in acetic acid (50 ml) was hydrogenated over a platinum oxide cataylst (0.5 g) at approximately 345 kilopascals pressure and room temperature for 3 hours (the theoretical uptake of hydrogen was observed). A small volume of $H_2O$ was added to dissolve the product and the catalyst was then filtered off. The filtrate was evaporated to dryness to yield an oil which crystallised under ether to yield 6-phenylsulphonamido-1,2,3,4-tetrahydroisoquinoline (1.63 g, 76%).

(g) To a refluxing solution of the product of (f) (0.8 g, 0.0028M) and triethylamine (0.3 g, 0.0028M) in $CH_3CN$ (30 ml) was added, dropwise over 1 hour, a mixture of ethylbromobutyrate (0.55 g, 0.0028M) and triethylamine (0.3 g, 0.0028M) in $CH_3CN$ (10 ml). The reaction mixture was refluxed for a further 2 hours and was then left for 48 hours at a room temperature. After evaporation to dryness, the residue was chromatographed in ethyl acetate on a silica gel column. Evaporation of the eluent yielded ethyl 4-[6-phenylsulphonamido-1,2,3,4-tetrahydroisoquinolin-2-yl]butyrate (0.5 g, 46%) as an oil.

(h) A mixture of the product of (g) (0.5 g, 0.0021M), 10% NaOH (10 ml) and 20 ml ethanol was stirred at room temperature for 1 hour and was then evaporated to dryness. The residue was dissolved in a small volume of $H_2O$ and dilute HCl was added to pH 6; the mixture was then extracted with $CH_2Cl_2$. The $CH_2Cl_2$ extracts were combined and dried over $MgSO_4$ and were then evaporated to dryness. THe residue was crystallised from an isopropanol:ether mixture to yield the title compound (0.14 g, 30%), m.p. 198°–200° C.

EXAMPLE 12

5-[7-Phenylsulphonamido-1,2,3,4-tetrahydroisoquiolin-2-yl]valeric acid (a) 1,2,3,4-Tetrahydroisoquinoline (50 g, 0.376M) was dissolved in concentrated $H_2SO_4$ (180 ml) with cooling. Solid potassium nitrate (40.4 g, 0.4M) was added in portions, keeping the temperature below 5° C., over 4 hours. The reaction mixture was allowed to stand overnight at room temperature and was then poured onto ice, basified with $NH_4OH$ and was then extracted with $CHCl_3$. After evaporation, the residue was dissolved in ethanol and concentrated HCl was added. The resulting precipitated hydrochloride salt was filtered off and recrystallized from methanol to yield 7-nitro-1,2,3,4-tetrahydroisoquinoline hydrochloride (31.5 g, 39%), m.p. 268°–269° C.

(b) A mixture of the product of (a) (31.5 g, 0.147M) and sodium acetate (12.0 g, 0.147M) in acetic anhydride (150 ml) was refluxed for 3 hours. After cooling, the mixture was poured onto ice and extracted with $CHCl_3$. After evaporation of the $CHCl_3$, the residue was recrystallised from ethyl acetate:ether to yield 2-acetyl-7-nitro-1,2,3,4-tetrahydroisoquinoline (24.4 g, 81%), m.p. 83°–4° C.

(c) A solution of the product of (b) (24.4 g, 0.119M) in ethanol (400 ml) was hydrogenated over 1% Palladium on charcoal catalyst at approximately 345 kilopascals pressure/room temperature for 5.5 hours. The catalyst was filtered off and the filtrate was evaporated. The residue was chromatographed in $CHCl_3$ on a silica gel column. Evaporation of the solvent yielded an oil which crystallised and was washed with ether to yield 2-acetyl-7-amino-1,2,3,4-tetrahydroisoquinoline (18.39 g, 88%), m.p. 108°–9° C. (lit.* 107°–9° C.).

*Ajao & Bird, *J. Het. Chem.*, 1985, 22, 329

(d) Benzenesulphonyl chloride (8.0 g, 0.046M) was added to the product of (c) (8.0 g, 0.046M) and pyridine (6.8 g, 0.086M) in $CH_2Cl_2$ (400 ml) over 15 minutes with cooling. The reaction mixture was left stirring overnight at room temperature and was then washed several times with $H_2O$. The $CH_2Cl_2$ solution was dried and evaporated and the residue was washed with $H_2O$ to yield 2-acetyl-7-phenylsulphonamido-1,2,3,4-tetrahydroisoquinoline (13.2 g, 91%), m.p. 180°–2° C.

(e) A mixture of the product of (d) (13.0 g, 0.041M), 3N HCl (150 ml) and n-butanol (50 ml) was refluxed for 3 hours and was then evaporated to dryness. The residue was recrystallised from isopropanol to yield 7-phenylsulphonamido-1,2,3,4-tetrahydroisoquinoline hydrochloride (11.57 g, 87%), m.p. 227°–8° C.

(f) To a refluxing mixture of the product of (e) (3.25 g, 0.01M) and triethylamine (1.01 g, 0.01M) in $CH_3CN$ (150 ml) was added a mixture of ethyl bromo valerate (2.09 g, 0.01M), triethylamine (1.01 g, 0.01M) in $CH_3CN$ (10 ml) over 3 hours. The reaction mixture was then refluxed for a further 2 hours and was then evaporated to dryness.

The residue was chromatographed in $CH_2Cl_2$:MeOH 10:1 on a silica gel column. Evaporation of the resulting fractions yielded a solid which was recrystallised from isopropanol:40–60 petroleum ether to give ethyl 5-[7-phenylsulphonamido-1,2,3,4-tetrahydroisoquinolin-2-yl]-valerate (1.8 g, 43%), m.p. 120°–121° C.

(g) 5-[(7-Phenylsulphonamido)-1,2,3,4-tetrahydroisoquinolin-2-yl]-valeric acid

A mixture of of the product of (f) (1.5 g, 0.0036M), 10% NaOH (10 ml) and ethanol (25 ml) was stirred at room temperature for 1 hour. The reaction mixture was then evaporated to dryness and the residue was dissolved in the minimum quantity of $H_2O$. The pH was adjusted to 6 with dilute HCl thereby causing a solid to precipiate out. The solid was filtered off and recrystallized from methanol to yield the title compound (0.69 g, 49.6%), m.p. 179°–180° C.

EXAMPLE 13

2-[(7-Phenylsulphonamido)-1,2,3,4-tetrahydroisiquinolin-2-yl]-acetic acid hydrochloride Using the method described in 12(f), the product of Example 12(e) (1.5 g, 0.0046M), was reacted with ethyl-bromoacetate (0.77 g, 0.0046M), in the presence of triethylamine (0.93 g, 0.009M) in $CH_3CN$ (50 ml) to yield the ethyl ester of the title compound as an oil 0.4 g (24%). The ester was converted to the title compound by the method described in Example 12(g) using 5 ml 10% NaOH in 10 ml ethanol. This gave the title compound (0.35 g, 83%), m.p. 165°–7° C.

EXAMPLE 14

2-[(7-Phenylsulphonamido)-1,2,3,4-tetrahydroisoquinolin-2-yl]-caproic acid hydrochloride Using the method described in Example 12(f), the product of Example 12(e) (1.7 g, 0.0035M), was reacted with ethyl bromohexanoate (1.2 g, 0.0053M), and triethylamine (1.07 g, 0.106M) in $CH_3CN$ (75 ml) to yield 1.44 g (63%) of the ethyl ester which was hydrolysed to the title compound by the method described in Example 12(g) using 10 ml 10% NaOH in 25 ml ethanol. This gave 0.75 g of the title compound, 58% yield, m.p. 210°–3° C.

EXAMPLE 15

4-[7-(4-Chlorophenylsulphamoyl)-1,2,3,4-tetrahydroisoquinolin-2-yl]butyric acid (a) Using the method described in Example 7, 2-acetyl-7-chlorosulphonyl-1,2,3,4-tetrahydroisoquinoline was reacted with 4-chloroaniline and the product was deacetylated to give 7-(4-chlorophenylsulphamoyl)-1,2,3,4-tetrahydroisoquinoline as the hydrochloride salt.

(b) The hydrochloride salt form (a) was reacted with ethyl 4-bromobutyrate according to the method described in Example 2(a) and the product was purified by elution from a silica column with ethyl acetate:methanol mixtures to give ethyl 4-[7-(4-chlorophenylsulphamoyl)-1,2,3,4-tetrahydroisoquinolin-2-yl]butyrate as a yellow oil.

(c) Ethyl 4-[7-(4-chlorophenylsulphamoyl)-1,2,3,4-tetrahydroisoquinolin-2-yl]butyrate was hydrolysed with sodium hydroxide solution by the method described in Example 2(b) and the product was recrystallised from ethanol to give the title compound, m.p. 210°–210.5° C.

EXAMPLE 16

2,2-Dimethyl-4-[7-(3-chlorophenylsulphamoyl)-1,2,3,4-tetrahydroisoquinolin-2-yl]butanoic acid Following the method of Example 2(a), substituting methyl-2,2-dimethyl-4-bromobutanoate (J. L. Bass et al, *Tetrahedron*, 1966, 22, 285) gave a mixture of methyl-2,2-dimethyl-4-[7-(3-chlorophenylsulphamoyl)-1,2,3,4-tetrahydroisoquinolin-2-yl]butanoate and 1-oxo-2,2-dimethyl-1,4-bis-[7-(3-chlorophenylsulphamoyl)-1,2,3,4-tetrahydroisoquinolin-2-yl]butane, which were separated by chromatography (silica gel, ether). The former compound was hydrolysed by the method of Example 2(b), substituting methanol for ethanol and carrying out the reaction for 24 hours, to give, after recrystallisation from ethanol, 2,2-dimethyl-4-[7-(3-chlorophenylsulphamoyl)-1,2,3,4-tetrahydroisoquinolin-2-yl]butanoic acid, 1.1 $C_2H_5OH$, 0.8 $H_2O$, m.p. ca. 120° C.

$C_{21}H_{25}ClN_2O_4S.1.1C_2H_5OH$, 0.8$H_2O$: Found: C 55.33 H 6.25 N 5.81. Requires: C 55.60 H 6.66 N 5.59.

EXAMPLE 17

Biological Activity

The compounds of Examples 1 to 16 were tested in the human platelet aggregation and human platelet binding assays as described above and the results obtained are shown in the Table below:

| Compound of Example No. | Human Platelet Aggregation IC$_{50}$ ($\mu$m) | Human Platelet Binding IC$_{50}$ ($\mu$m) |
| --- | --- | --- |
| 1 | 103 | 49.3 |
| 2 | 9.3 | 1.02 |
| 3a | — | 3.1 |
| 3b | 3.9 | 1.06 |
| 4 | 34 | 3.8 |
| 5 | — | 3.75 |
| 6 | — | 9.2 |
| 7 | — | 2.8 |
| 8 | — | 0.7 |
| 9 | — | 79 |
| 10 | — | 134 |
| 11 | — | 232 |
| 12 | — | 40.7 |
| 13 | — | 84 |
| 14 | — | 98 |
| 15 | — | 7.8 |
| 16 | — | — |

We claim:

1. A compound of the formula (I):

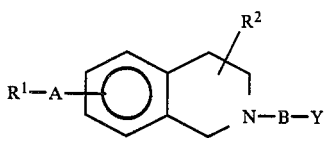

and salts thereof; wherein

A is a group NR$^3$SO$_2$ or SO$_2$NR$^3$;

B is an acyclic hydrocarbon group having from one to six linear carbon atoms, provided that the carbon atom attached to the nitrogen is saturated;

Y is CO$_2$H or a group hydrolysable to CO$_2$H;

R$^1$ is phenyl optionally substituted by one or more substituents chosen from the group consisting of halogen, C$_{1-4}$alkyl, C$_{1-6}$acyl, C$_{1-4}$alkoxy, nitro and trifluoromethyl;

R$^2$ is hydrogen or one or more C$_{1-4}$alkyl substituents located at the 1, 3 and 4 positions of the isoquinoline ring; and R$^3$ is hydrogen or C$_{1-6}$alkyl.

2. A compound according to claim 1 wherein Y is CO$_2$H or a C$_{1-4}$alkyl ester derivative thereof.

3. A compound according to claim 1 wherein A is NHSO$_2$.

4. A compound according to claim 1 wherein R$^1$ is selected from the group consisting of unsubstituted phenyl or phenyl substituted with chloro, bromo, methyl, trifluoromethyl and methoxy.

5. A compound according to claim 4 wherein R$^1$ is 3-chlorophenyl.

6. A compound according to claim 1 wherein B is selected from the group consisting of propane-1,3-diyl, butane-1,4-diyl and prop-1-yne-1,3-diyl.

7. A compound of the formula (II):

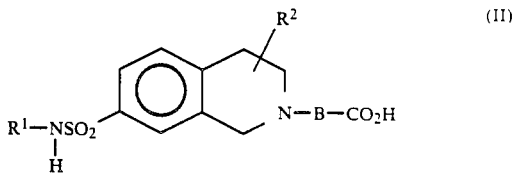

and salts and C$_{1-4}$alkyl esters thereof; wherein

B is an acyclic hydrocarbon group having from one to six linear carbon atoms, provided that the carbon atom attached to the nitrogen atom is saturated;

R$^1$ is phenyl optionally substituted by one or more substituents chosen from the group consisting of halogen, C$_{1-4}$alkyl, C$_{1-6}$acyl, C$_{1-4}$alkoxy, nitro and trifluoromethyl; and R$^2$ is hydrogen or one or more C$_{1-4}$alkyl substituents located at the 1, 3 and 4 positions of the isoquinoline ring.

8. A compound according to claim 7 wherein R$^2$ is hydrogen.

9. A compound according to claim 8 wherein R$^1$ is selected from the group consisting of unsubstituted phenyl or phenyl substituted with chloro, bromo, methyl, trifluoromethyl and methoxy.

10. A compound according to claim 9 wherein R$^1$ is 3-chlorophenyl.

11. 4-[7-(3-Chlorophenylsulphamoyl)-1,2,3,4-tetrahydroisoquinolin-2-yl]butanoic acid.

12. 5-[7-(3-Chlorophenylsulphamoyl)-1,2,3,4-tetrahydroisoquinolin-2-yl]pentanoic acid.

13. 4-[7-(3-Chlorophenylsulphamoyl)-1,2,3,4-tetrahydroisoquinolin-2-yl]but-1-ynoic acid.

14. A pharmaceutical composition comprising, in a non-toxic amount effective to antagonise thromboxane A$_2$ receptors, a compound as defined in claim 2, and a pharmaceutically acceptable carrier.

15. A pharmaceutical composition comprising, in a non-toxic amount effective to antagonise thromboxane A$_2$ receptors, a compound as defined in claim 7, and a pharmaceutically acceptable carrier.

16. A method of treating thromboxane A$_2$ mediated diseases in a patient, which method comprises administering to said patient a non-toxic therapeutically effective thromboxane A$_2$ receptor antagonist amount of a compound as defined in claim 2.

17. A method of treating thromboxane A$_2$ mediated diseases in a patient, which method comprises administering to said patient a non-toxic therapeutically effective thromboxane A$_2$ receptor antagonist amount of a compound as defined in claim 7.

* * * * *